(12) United States Patent
Miyai et al.

(10) Patent No.: US 10,319,088 B2
(45) Date of Patent: Jun. 11, 2019

(54) INSPECTION APPARATUS OF EUV MASK AND ITS FOCUS ADJUSTMENT METHOD

(71) Applicant: Lasertec Corporation, Yokohama (JP)

(72) Inventors: Hiroki Miyai, Yokohama (JP); Kiwamu Takehisa, Yokohama (JP)

(73) Assignee: Lasertec Corporation, Yokohama (JP)

( * ) Notice: Subject to any disclaimer, the term of this patent is extended or adjusted under 35 U.S.C. 154(b) by 69 days.

(21) Appl. No.: 15/441,633

(22) Filed: Feb. 24, 2017

(65) Prior Publication Data

US 2017/0256045 A1 Sep. 7, 2017

(30) Foreign Application Priority Data

Mar. 2, 2016 (JP) .................................. 2016-039598

(51) Int. Cl.
| | |
|---|---|
| *H04N 19/124* | (2014.01) |
| *G01N 21/88* | (2006.01) |
| *G06T 7/00* | (2017.01) |
| *G01N 21/956* | (2006.01) |
| *H04N 5/225* | (2006.01) |
| *G03F 1/84* | (2012.01) |

(52) U.S. Cl.
CPC ....... *G06T 7/0004* (2013.01); *G01N 21/8806* (2013.01); *G01N 21/956* (2013.01); *G03F 1/84* (2013.01); *H04N 5/2256* (2013.01); *G01N 2021/95676* (2013.01); *G06T 2207/10148* (2013.01); *G06T 2207/30148* (2013.01)

(58) Field of Classification Search
CPC ..... G01N 2021/95676; G01N 21/8806; G01N 21/956; G06T 2207/10148; G06T 2207/30148; G06T 7/0004; H04N 5/2256
See application file for complete search history.

(56) References Cited

U.S. PATENT DOCUMENTS

| | | | | |
|---|---|---|---|---|
| 9,915,621 | B2 * | 3/2018 | Foad | G01N 21/95 |
| 2008/0113491 | A1 * | 5/2008 | Wood | B82Y 10/00 |
| | | | | 438/460 |
| 2015/0205193 | A1 | 7/2015 | Yamada et al. | |

FOREIGN PATENT DOCUMENTS

| | | | |
|---|---|---|---|
| JP | 2000199856 A | | 7/2000 |
| JP | 2008191476 | * | 8/2008 |
| JP | 2008191476 A | | 8/2008 |

(Continued)

OTHER PUBLICATIONS

Japan Patent Office, Office Action Issued in Application No. 2016-039598, dated Jun. 14, 2016, 9 pages.

*Primary Examiner* — Jessica M Prince
(74) *Attorney, Agent, or Firm* — McCoy Russell LLP (57) ABSTRACT

An inspection apparatus according to an aspect of the present invention includes an EUV light source 11, an illumination optical system 10 provided to apply the EUV light to an EUV mask 60, a concave mirror and a convex mirror 22 configured to reflect the EUV light reflected on the EUV mask 60, a camera 32 configured to detect EUV light reflected on the convex mirror 22 and thereby take an image of the EUV mask 60, an AF light source 16 configured to generate AF light having a wavelength of 450 nm to 650 nm, first and second detectors 27 and 30 configured to detect the AF light reflected on the EUV mask 60 through the concave mirror with the hole 21 and the convex mirror 22, and an processing device 31 configured to adjust a focus point of the EUV light on the EUV mask 60.

14 Claims, 5 Drawing Sheets

(56) References Cited

FOREIGN PATENT DOCUMENTS

| JP | 2014153326 | * | 8/2014 |
|---|---|---|---|
| JP | 2014153326 A | | 8/2014 |
| JP | 2014235365 A | | 12/2014 |
| JP | 2015156014 A | | 8/2015 |

* cited by examiner

INSPECTION APPARATUS OF EUV MASK AND ITS FOCUS ADJUSTMENT METHOD

CROSS REFERENCE TO RELATED APPLICATIONS

The present application claims priority to Japanese Patent Application No. 2016-039598, filed on Mar. 2, 2016, the entire contents of which are hereby incorporated by reference in their entirety for all purposes.

BACKGROUND OF THE INVENTION

Field of the Invention

The present invention relates to an inspection apparatus for an EUV mask and its focus adjustment method.

Description of Related Art

For a lithography technology that plays an important role in the miniaturization of semiconductor devices, ArF lithography in which an ArF excimer laser having an exposure wavelength of 193 nm is used as an exposure light source is currently used for mass-production. Further, an immersion technique (also called "ArF immersion lithography") for increasing the resolution of an exposure device by filling a space between its objective lens and a wafer with water has also begun to be used for mass production. In order to advance the miniaturization of semiconductor devices even further, development of various techniques for putting EUVL (Extremely Ultraviolet Lithography) having an exposure wavelength of 13.5 nm to practical use has been in progress.

The minimum size and the depth of a defect that is unacceptable for an EUV mask, especially for a substrate or blanks, have become greatly smaller compared to those for conventional ArF masks. Because of this fact, the detection of a defect has been becoming more difficult. Accordingly, it has been considered that by performing an inspection by using EUV light, i.e., illumination light having the same wavelength as that of the exposure light, namely, a wavelength of 13.5 nm, a microscopic irregularity defect (such as a bump and a dent) of about one tenth of the wavelength can be detected. An inspection using the same wavelength as that of the exposure light is called an "Actinic inspection".

Japanese Unexamined Patent Application Publication No. 2014-235365 discloses a method for adjusting a focus in an inspection apparatus for an EUV mask. In Japanese Unexamined Patent Application Publication No. 2014-235365, a pattern for focusing (hereinafter referred to as a "focusing pattern") whose size is known is formed on an EUV mask. Then, an image of the focusing pattern is taken through a non-telecentric magnification optical system.

However, in the method disclosed in Japanese Unexamined Patent Application Publication No. 2014-235365, it is necessary to form a focusing pattern having a known size on the EUV mask.

The present invention has been made in view of the above-described circumstances and an object thereof is to provide an inspection apparatus capable of appropriately adjusting a focus point with a simple configuration and its focus adjustment method.

SUMMARY OF THE INVENTION

A first exemplary aspect is an inspection apparatus including: an EUV (Extremely Ultraviolet) light source configured to generate EUV light; an illumination optical system provided to apply the EUV light to an EUV mask including a multilayer reflection film and an absorption film; a concave mirror with a hole formed therein, the concave mirror with the hole being configured to reflect the EUV light reflected on the EUV mask; a convex mirror configured to reflect the EUV light reflected on the concave mirror with the hole toward the hole of the concave mirror with the hole; an image pickup device configured to detect the EUV light reflected on the convex mirror and thereby take an image of the EUV mask; an AF light source configured to generate AF light having a wavelength of 450 nm to 650 nm; an AF photodetector configured to detect the AF light reflected on the EUV mask through the concave mirror with the hole and the convex mirror; and an adjustment unit configured to adjust a focus point of the EUV light on the EUV mask based on a detection result of the AF photodetector. By the above-described configuration, it is possible to appropriately adjust a focus with a simple configuration.

In the above-described inspection apparatus, the AF light may be incident on an outer side of an incident place of the EUV light on a reflection surface of the concave mirror with the hole. In this way, it is possible to relax a required accuracy of the shape of the concave mirror with the hole.

In the above-described inspection apparatus, the illumination optical system may include a dropping mirror disposed directly above the EUV mask, the dropping mirror being configured to reflect the EUV light emitted from the EUV light source toward the EUV mask, and the AF light may be reflected on the dropping mirror and then incident on the EUV mask. By the above-described configuration, it is possible to adjust the focus with a simple configuration.

In the above-described inspection apparatus, a stop may be disposed in a place conjugate with the EUV mask in the illumination optical system, and the AF light source may be disposed on a rear side of the stop. By the above-described configuration, it is possible to adjust the focus with a simple configuration.

In the above-described inspection apparatus, the illumination optical system may include a dropping mirror disposed directly above the EUV mask, the dropping mirror being configured to reflect the EUV light emitted from the EUV light source toward the EUV mask, and the AF light may be incident on the EUV mask from outside of the dropping mirror. By the above-described configuration, it is possible to adjust the focus with a simple configuration.

In the above-described inspection apparatus, an incident place of the AF light may coincide with the incident place of the EUV light on the EUV mask. By the above-described configuration, it is possible to adjust the focus that is located in the same place as an inspection area.

In the above-described inspection apparatus, an incident place of the AF light may be deviated from the incident place of the EUV light on the EUV mask. By the above-described configuration, it is possible to adjust the focus with a simple configuration.

In the above-described inspection apparatus, a pellicle formed of a material containing silicon may be provided on the EUV mask. Since a wavelength with which light has a high transmittance for the pellicle is used, it is possible to prevent the amount of detected light from being reduced.

A focus adjustment method according to an aspect of an exemplary embodiment is a focus adjustment method for an inspection apparatus, the inspection apparatus including: an EUV light source configured to generate EUV light; an illumination optical system provided to apply the EUV light to an EUV mask including a multilayer reflection film and an absorption film; a concave mirror with a hole formed therein, the concave mirror with the hole being configured to reflect the EUV light reflected on the EUV mask; a convex mirror configured to reflect the EUV light reflected on the concave mirror with the hole toward the hole of the concave mirror with the hole; an image pickup device configured to detect the EUV light reflected on the convex mirror and thereby take an image of the EUV mask; and an AF light source configured to generate AF light having a wavelength of 450 nm to 650 nm, the focus adjustment method including: a step of detecting the AF light reflected on the EUV mask through the concave mirror with the hole and the convex mirror; and a step of adjusting a focus point of the EUV light on the EUV mask based on a detection result of the AF photodetector. By the above-described configuration, it is possible to appropriately adjust a focus with a simple configuration.

In the above-described focus adjustment method, the AF light may be incident on an outer side of an incident place of the EUV light on a reflection surface of the concave mirror with the hole. In this way, it is possible to relax the required accuracy of the shape of the concave mirror with the hole.

In the above-described focus adjustment method, the illumination optical system may include a dropping mirror disposed directly above the EUV mask, the dropping mirror being configured to reflect the EUV light emitted from the EUV light source toward the EUV mask, so that the AF light is reflected on the dropping mirror and then incident on the EUV mask. By the above-described configuration, it is possible to adjust the focus with a simple configuration.

In the above-described focus adjustment method, a stop may be disposed in a place conjugate with the EUV mask and the AF light source may be disposed on a rear side of the stop in the illumination optical system.

In the above-described focus adjustment method, the illumination optical system may include a dropping mirror disposed directly above the EUV mask, the dropping mirror being configured to reflect the EUV light emitted from the EUV light source toward the EUV mask, so that the AF light is incident on the EUV mask from outside of the dropping mirror. By the above-described configuration, it is possible to adjust the focus with a simple configuration.

In the above-described focus adjustment method, an incident place of the AF light may coincide with the incident place of the EUV light in the EUV mask. By the above-described configuration, it is possible to adjust the focus that is located in the same place as an inspection area.

In the above-described focus adjustment method, the incident place of the AF light may be deviated from the incident place of the EUV light in the EUV mask. By the above-described configuration, it is possible to adjust the focus with a simple configuration.

In the above-described focus adjustment method, a pellicle formed of a material containing silicon may be provided on the EUV mask. Since a wavelength at which light has a high transmittance for the pellicle is used, it is possible to prevent the amount of detected light from being reduced.

According to the present invention, it is possible to provide an inspection apparatus capable of appropriately adjusting a focus point with a simple configuration and its focus adjustment method. The above and other objects, features and advantages of the present invention will become more fully understood from the detailed description given hereinbelow and the accompanying drawings which are given by way of illustration only, and thus are not to be considered as limiting the present invention.

DESCRIPTION OF THE EXEMPLARY EMBODIMENTS

First Exemplary Embodiment

Figure 1:
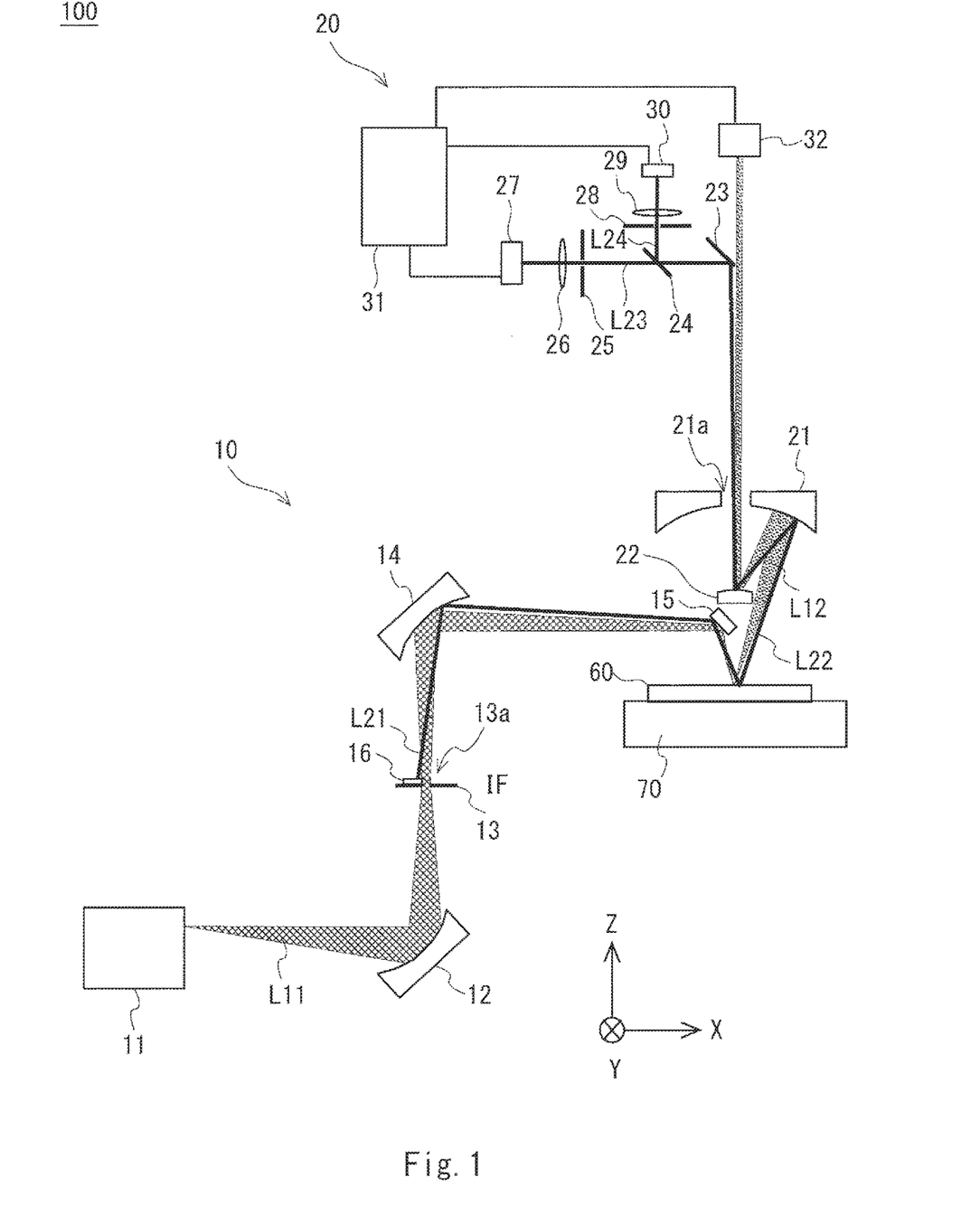
FIG. 1 shows a configuration of an inspection apparatus according to a first exemplary embodiment.

Exemplary embodiments according to the present invention are explained hereinafter with reference to the drawings. Firstly, an overall configuration of an inspection apparatus according to this exemplary embodiment is explained with reference to FIG. 1. FIG. 1 shows an optical system of an inspection apparatus 100 for inspecting an EUV mask 60.

The inspection apparatus 100 includes an illumination optical system 10, a detection optical system 20, a processing device 31, a camera 32, and a stage 70. The illumination optical system 10 includes an EUV light source 11, a concave mirror 12, a stop 13, a concave mirror 14, and a dropping mirror 15. The detection optical system 20 includes a concave mirror with a hole formed therein (hereinafter also referred to as a "concave mirror with hole") 21, a convex mirror 22, a mirror 23, a half mirror 24, a slit 25, a lens 26, a first detector 27, a slit 28, a lens 29, and a second detector 30.

The inspection apparatus 100 includes an inspection optical system for inspecting an EUV mask 60, and an AF (Auto Focus) optical system for focusing illumination light on the EUV mask 60. Firstly, the inspection optical system is explained.

The EUV light source 11 generates EUV light L11 having a wavelength of 13.5 nm, which is equal to the exposure wavelength for the EUV mask 60 to be inspected. The EUV light L11 generated by the EUV light source 11 is reflected on the concave mirror 12. The EUV light L11 reflected on the concave mirror 12 travels while its thickness (or width) is becoming narrower (i.e., as the EUV light L11 reflected on the concave mirror 12 travels, it becomes narrower), and then is incident on the stop 13. The stop 13 has an aperture 13a for letting the light pass therethrough on the optical axis of the EUV light L11. Therefore, the EUV light L11 passes through the aperture 13a of the stop 13. Note that the stop 13 is disposed in the intermediate focal point (i.e., the intermediate concentration point) IF of the EUV light L11 concentrated by the concave mirror 12. The intermediate focal point IF is disposed in a place conjugate with a patterned surface of the EUV mask 60.

The EUV light L11 that has passed through the stop 13 travels while its thickness (or width) is becoming wider, and then is incident on the concave mirror 14. The EUV light L11 reflected on the concave mirror 14 travels while its thickness is becoming narrower, and then is incident on the dropping mirror 15. The dropping mirror 15 is disposed directly above the EUV mask 60. Then, the EUV light L11 reflected on the dropping mirror 15 is incident on the EUV mask 60. The concave mirror 14 concentrates the EUV light L11 on the EUV mask 60. The EUV light L11 serves as illumination light for illuminating the EUV mask 60.

The EUV mask 60 is placed on the stage 70. Here, a plane in parallel with the top surface of the EUV mask 60 is defined as an "XY-plane" and a direction perpendicular to the XY-plane is defined as a "Z-direction". The EUV light L11 is incident on the EUV mask 60 in a direction that is inclined from the Z-direction. That is, the EUV light L11 is obliquely-incident on the EUV mask 60 and illuminates the EUV mask 60. In this example, the EUV light L11 is obliquely-incident on the EUV mask 60 in a direction inclined in the X-direction. The stage 70 is an XYZ-drive stage. It is possible to illuminate a desired area on the EUV mask 60 by moving the stage 70 in the XY-directions. Further, it is possible to adjust the focus by moving the stage 70 in the Z-direction. The processing device 31 serves as an adjustment unit that controls the stage 70 and thereby adjusts the focus.

Figure 2:
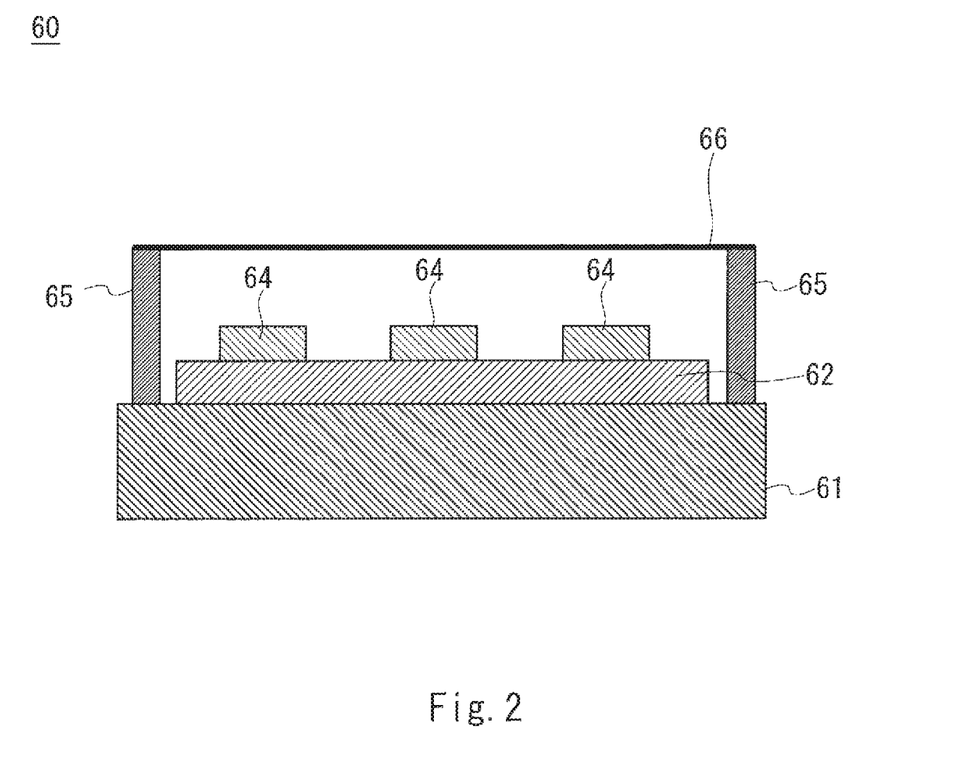
FIG. 2 schematically shows a cross-sectional structure of an EUV mask to be inspected.

A configuration of the EUV mask 60 to be inspected is explained hereinafter with reference to FIG. 2. FIG. 2 is a cross section schematically showing the configuration of the EUV mask 60. The EUV mask 60 includes a substrate 61, a multilayer reflection film 62, an absorption film 64, a frame 65 and a pellicle 66.

The substrate 61 is formed of low-heat expansion glass. The multilayer reflection film 62, which is used to reflect the EUV light, is disposed on the substrate 61. The multilayer reflection film 62 typically has a structure in which molybdenum layers and silicon layers are alternately laminated several tens of times. The multilayer reflection film 62 can reflect about 65% of the EUV light having the wavelength of 13.5 nm when the EUV light is incident at the right angle. The absorption film 64, which absorbs the EUV light, is disposed on this multilayer reflection film 62 and blanks are thereby formed. The absorption film 64 is formed of, for example, TaBN. By patterning the absorption film 64 (i.e., by shaping the absorption film 64 into a desired pattern), an EUV mask 60 with a pattern formed thereon is completed. Note that a protection film (films called a "buffer layer" and a "capping layer") may be interposed between the absorption film 64 and the multilayer reflection film 62.

Further, the pellicle frame 65 is provided above the substrate 61. The pellicle frame 65 is disposed on a peripheral part of the EUV mask 60. That is, the pellicle frame 65 is disposed so as to surround an exposure area in which the pattern of the absorption film 64 is formed. The pellicle 66 is provided in a tensioned state on the surface of the pellicle frame 65 opposite to the patterned surface. That is, the pellicle 66 is disposed in a place that is apart from the patterned surface by a distance corresponding to the height of the pellicle frame 65. The pellicle 66 is formed of a material containing silicon. Specifically, the pellicle 66 may be a silicon film having a thickness of 50 nm. As described above, the pellicle 66 covers the exposure area in which the absorption film 64 is formed.

The explanation is continued by referring to FIG. 1 again. The EUV light L11 emitted from the EUV light source 11 illuminates an inspection area of the EUV mask 60. The size of the inspection area illuminated by the EUV light L11 is about 0.5 mm square. The EUV light L11 reflected on the EUV mask 60 is incident on the concave mirror with hole 21. A hole 21a is formed at the center of the concave mirror with hole 21. The EUV light L11 reflected on the concave mirror with hole 21 is incident on the convex mirror 22 and the convex mirror 22 reflects the EUV light L11, which has come from the concave mirror with hole 21, toward the hole 21a of the concave mirror with hole 21. The EUV light L12, which has passed through the hole 21a of the concave mirror with hole 21, is detected by the camera 32. The camera 32 is an image pickup device such as a CCD (Charge Coupled Device) sensor, a CMOS (Complementary Metal Oxide Semiconductor) sensor, and a TDI (Time Delay Integration) sensor, and takes an image of the EUV mask 60.

The image taken by the camera 32 is output from the camera 32. In this way, it is possible to inspect whether the EUV mask 60 is defective or not. Specifically, the concave mirror with hole 21 and the convex mirror 22 form a Schwarzschild magnification optical system. Therefore, the inspection area is projected onto the camera 32 in an enlarged size by the EUV light L11. When there is a defect in the minute inspection area, scattered light occurs. Therefore, it is possible to detect a defect by taking an image of the EUV mask 60.

Next, an AF optical system for adjusting a focus is explained. An AF light source 16 generates AF light L21 that is used for adjusting the focus. The AF light L21 is light having a wavelength different from that of the EUV light L11. Specifically, the AF light L21 is preferably visible light having a wavelength of 450 nm to 650 nm. More preferably, the AF light L21 is visible light having a wavelength equal to or close to 500 nm. For example, the AF light source 16 may be an LED (Light Emitting Diode), a laser diode, an optical fiber, or the like, and is preferably a point source of light.

For example, the AF light source 16 is disposed on the rear side of the stop 13 (i.e., on or near the rear surface of the stop 13). That is, the AF light source 16 is disposed on the concave mirror 14 side of the stop 13. The AF light source 16 is disposed outside of the aperture of the stop 13. Therefore, the AF light L21 propagates along an optical axis that is different from the optical axis of the EUV light L11. That is, the optical axis of the AF light L21 is inclined from the optical axis of the EUV light L11.

The AF light L21 emitted from the AF light source 16 is reflected on the concave mirror 14 and the dropping mirror 15, and then is incident on the EUV mask 60. The optical axis of the AF light L21 is inclined from the Z-direction. Therefore, the AF light L21 is obliquely-incident on the EUV mask 60. Further, the optical axis of the AF light L21 is deviated from the optical axis of the EUV light L11. Therefore, the AF light L21 is incident on a place that is different from the place on which the EUV light L11 is incident. That is, on the EUV mask 60, the incident place on which the AF light L21 is incident is deviated from the place on which the EUV light L11 is incident. In other words, on the patterned surface of the EUV mask 60, the spot of the EUV light L11 (i.e., the spot where the EUV light L11 is incident) does not overlap the spot of the AF light L21. As described above, the AF light L21 is incident on a place outside of the inspection area illuminated by the EUV light L11.

Similarly to the EUV light L12, the AF light L22 reflected on the EUV mask 60 is reflected on the concave mirror with hole 21 and the convex mirror 22. That is, the AF light L22 reflected on the EUV mask 60 is incident on the concave mirror with hole 21. Note that when the EUV light and the AF light are regularly-reflected on the normal places of the EUV mask 60, the incident place of the AF light L22 is located on the outer side of the incident place of the EUV light L12 on the reflection surface of the concave mirror with hole 21. That is, the EUV light L12 is incident on a place that is closer to the hole 21a than the place where the AF light L22 is incident is to the hole 21a.

The AF light L22 is reflected on the concave mirror with hole 21 and is incident on the convex mirror 22. The convex mirror 22 reflects the AF light L22 toward the hole 21a of the concave mirror with hole 21. The AF light L22, which has passed through the hole 21a of the concave mirror with hole 21, is incident on the mirror 23.

The mirror 23 is disposed in a place on which only the AF light L22 is incident and the EUV light L12 is not incident. That is, the mirror 23 is located outside of the optical path of the EUV light L12. As described previously, the optical axis of the EUV light L12 differs from the optical axis of the AF light L11. Therefore, the optical axis of the AF light L21 reflected on the EUV mask 60 also differs from the optical axis of the EUV light L12 reflected on the EUV mask 60. By using such a configuration, it is possible to separate the optical path of the AF light L22 from the optical path of the EUV light L12. In this way, the AF light L22 is detected by an optical detector different from the camera 32 as described later. Needless to say, the mirror 23 may be disposed so that it reflects only the EUV light L12, rather than reflecting only the AF light L22. It should be noted that by using the configuration in which the mirror 23 reflects the AF light L22, instead of reflecting the EUV light L12, a mirror having a higher reflectivity can be used as the mirror 23.

The AF light L22 reflected on the mirror 23 is branched into two light beams by the half mirror 24. Hereinafter, the two beams branched by the half mirror 24 are referred to as "AF light L23" and "AF light L24". The AF light L23, which has passed through the half mirror 24, passes through the slit 25 and is incident on the lens 26. The lens 26 concentrates the AF light L23 on a light-receiving surface of the first detector 27. The first detector 27 detects the AF light L23 concentrated by the lens 26. The first detector 27 is, for example, a photodiode. The first detector 27 outputs a first detection signal, which changes according to the amount of detected AF light L23, to the processing device 31.

The AF light L24 reflected on the half mirror 24 passes through the slit 28 and is incident on the lens 29. The lens 29 concentrates the AF light L24 on a light-receiving surface of the second detector 30. The second detector 30 detects the AF light L24 concentrated by the lens 29. The second detector 30 is, for example, a photodiode. The second detector 30 outputs a second detection signal, which changes according to the amount of detected AF light L24, to the processing device 31. In this way, the first and second detectors 27 and 30 detect the EUV light reflected on the EUV mask 60 through the concave mirror with hole 21 and the convex mirror 22.

The distance from the half mirror 24 to the slit 25 differs from the distance from the half mirror 24 to the slit 28. Specifically, the distance from the half mirror 24 to the slit 25 is longer than the distance from the half mirror 24 to the slit 28. Further, the slit 28 is located in front of the focal point of the AF light by the concave mirror with hole 21 and the convex mirror 22, and the slit 25 is located behind the focal point of the AF light. Therefore, the amount of light detected by the second detector 30 (hereinafter referred to as the "detected light amount" of the second detector 30) is maximized when the slit 28 is in a front-focus state (i.e., a state where the focal point is located in front of the subject) and the detected light amount of the first detector 27 is maximized when the slit 28 is in a rear-focus state (i.e., a state where the focal point is located behind the subject).

For example, the slits 25 and 28 are arranged so that when the EUV mask 60 is located in the focused focal point of the EUV light L11, the detected light amounts of the first and second detectors 27 and 30 are equal to each other. Further, as the position of the EUV mask 60 is deviated from the focused focal point, the detected light amount of one of the first and second detectors 27 and 30 increases and the detected light amount of the other detector decreases. Further, which of the detectors becomes the detector whose detected light amount increases is determined depending on the direction in which the EUV mask 60 is deviated from the focused focal point. It is possible to detect the deviation of the position of the EUV mask 60 from the focal point by having the processing device 31 compare the first and second detection signals.

For example, the processing device 31 obtains (or calculates) a ratio between the first and second detection signals. Then, the processing device 31 drives the stage 70 according to the ratio between the detection signals. That is, the processing device 31 drives the stage 70 in the Z-direction and the height of the position of the EUV mask 60 is thereby changed. Therefore, the focal point can be adjusted. By doing so, the focus point can be accurately adjusted. The processing device 31 adjusts the focus based on detection results in the first and second detectors 27 and 30. For example, the processing device 31 performs feedback control for the stage 70 so that the first and second detection signals become equal to each other. By doing so, the camera 32 takes an image of the EUV mask 60 in the focused focal point. As a result, it is possible to accurately detect a defect.

Note that in the above explanation, the focus point is adjusted by disposing the slit 28 in the front-focus position and disposing the slit 25 in the rear-focus position. However, the configuration for adjusting the focus is not limited to the above-described configuration. For example, the focus point is adjusted by using an optical lever method.

Figure 3:
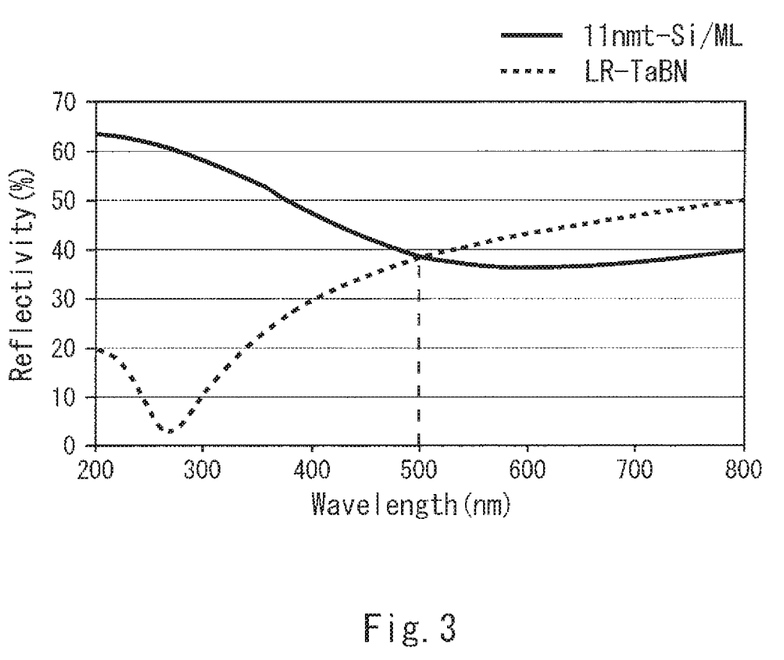
FIG. 3 is a graph showing reflectivity on an EUV mask.

The reason for using the visible light having a wavelength of 450 nm to 650 nm as the AF light L21 is explained hereinafter. FIG. 3 is a graph showing reflectivity of the multilayer reflection film 62 and the absorption film 63. In FIG. 3, the horizontal axis indicates wavelengths and the vertical axis indicates reflectivity. Further, a solid line indicates the reflectivity of the multilayer reflection film 62 and a broken line indicates the reflectivity of the absorption film 63 in FIG. 3.

In a range of wavelengths from 450 nm to 650 nm, the reflectivity of the multilayer reflection film 62 and that of the absorption film 63 are roughly equal to each other. Therefore, the EUV mask 60 has a reflective characteristic in which the intensity of regularly-reflected light is roughly unchanged regardless of the presence/absence of the pattern of the absorption film 63. By using the AF light L21 having the above-described wavelength, the effect caused by the presence/absence of the pattern of the absorption film 63 can be reduced.

Assume an example case in which the absorption film 63 is patterned (i.e., shaped into a desired pattern) on the EUV mask 60. The AF light L21 is reflected on the absorption film 63 in places where the absorption film 63 is formed. The AF light L21 is reflected on the multilayer reflection film 62 in places where the absorption film 63 is not formed. The reflectivity of light having a wavelength of 450 nm to 650 nm for the absorption film 63 is roughly equal to the reflectivity for the multilayer reflection film 62. Therefore, the contrast between the multilayer reflection film 62 and the absorption film 63 is low. The change in the amount of light caused by the presence/absence of the pattern can be reduced by using AF light that does not include wavelengths other than the wavelength of 450 nm to 650 nm. As a result, the focus can be adjusted more accurately. Therefore, it is possible to appropriately adjust the focus with a simple configuration.

Further, the intensity of scattered light reflected on the surface of the EUV mask 60 is in inverse proportion to the fourth power of the wavelength. Therefore, by using AF light having a wavelength longer than that of the EUV light, the increase in the error caused by the scattered light is improved (i.e., reduced). Therefore, it is possible to accurately adjust the focus.

Figure 4:
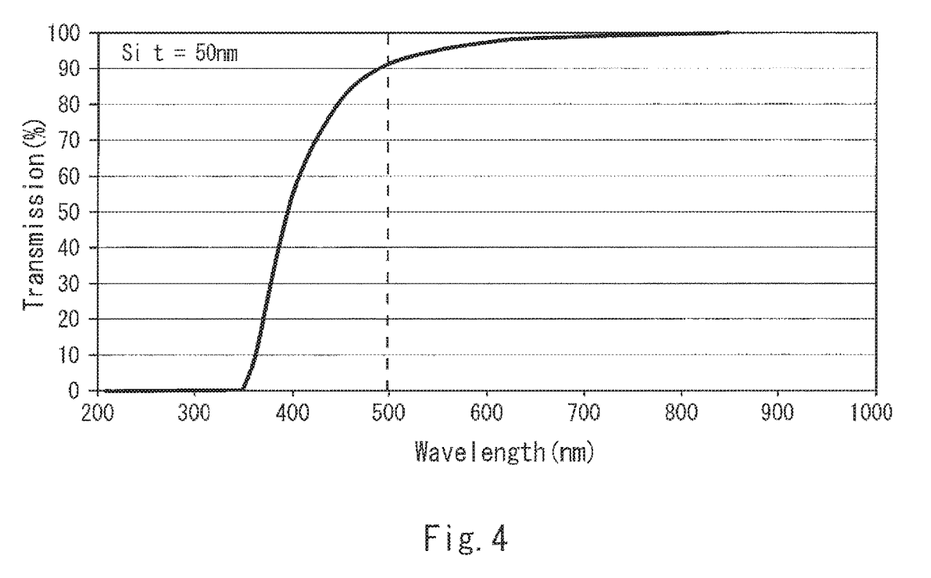
FIG. 4 is a graph showing transmittance of pellicle.

FIG. 4 is a graph showing transmittance (or transmission) of the pellicle 66. As shown in FIG. 4, when the wavelength is around 500 nm, the transmittance of the pellicle 66 is high. Therefore, it is possible to prevent the amount of the AF light L22 detected by the detector from being lowered. Accordingly, by using the AF light source 16 having a wavelength of 450 nm to 650 nm, the first and second detectors 27 and 30 can detect sufficient amounts of the AF light L23 and L24, respectively. Needless to say, the AF light may include wavelengths other than the wavelength of 450 to 650 nm. Further, a wavelength filter may be used so that only AF light having an appropriate wavelength passes therethrough.

Further, in this exemplary embodiment, the AF light source 16 is disposed on the rear side of the stop 13, which is located in the intermediate focal point IF. The intermediate focal point IF is disposed in a place conjugate with the EUV mask 60. Therefore, it is possible to bring the incident places of the AF light L21 and the EUV light L11 on the EUV mask 60 close to each other by disposing the AF light source 16 near the aperture 13a of the stop 13. In this way, it is possible to adjust the focal point based on the AF light that is reflected on the incident place close to the inspection area. Therefore, it is possible to accurately adjust the focus. Since the inspection can be carried out in the focused focal point, a defect can be detected more accurately. Therefore, it is possible to appropriately adjust the focus with a simpler configuration.

Further, the AF light L22 is incident on the outer side of the incident place of the EUV light L12 on the reflection surface of the concave mirror with hole 21. That is, on the reflection surface of the concave mirror with hole 21, the incident place of the EUV light L12 is closer to the hole 21a that the incident place of the AF light L22 is to the hole 21a. By this configuration, it is possible to use the inner NA area of the concave mirror with hole 21, which serves as the objective mirror, for the image-formation optical system using the EUV light and use the outer NA area of the concave mirror with hole 21 for the AF optical system. The EUV light has a short wavelength. Therefore, to make the phase of an image uniform (or aligned) and improve the resolution thereof, it is necessary to improve the accuracy of the shape (hereinafter referred to as the "shape accuracy") of the concave mirror with hole 21.

In this exemplary embodiment, only the inner NA area of the concave mirror with hole 21 is used for the image formation using the EUV light L12. Therefore, it is necessary to construct (or form) only the inner NA area of the concave mirror with hole 21 with high shape accuracy. In other words, the outer NA area of the concave mirror with hole 21 may be constructed (or shaped) with low shape accuracy. That is, since only the ratio between the detected light amounts of the first and second detectors 27 and 30 is monitored for the focus adjustment, the design aberration and the shape accuracy of the outer NA area can be relaxed. Therefore, the outer NA area of the concave mirror with hole 21 can be constructed (or formed) with shape accuracy lower than that of the inner NA area thereof. Therefore, there is no need to construct (or form) the whole concave mirror with hole with high shape accuracy.

For example, an NA area that is located on the inner side of an NA of 0.27 is used for the image formation using the EUV light. The NA area located on the outer side of the NA of 0.27 has a large aberration and hence is used only for a relay of the AF optical system. By using the above-described configuration, an area having a high NA can be used, thus making it possible to raise the contrast of the focus adjustment. Further, since the shape accuracy of only the inner NA area of the concave mirror with hole 21 needs to be increased, the cost for the component used as the concave mirror with hole 21 can be reduced.

Second Exemplary Embodiment

Figure 5:
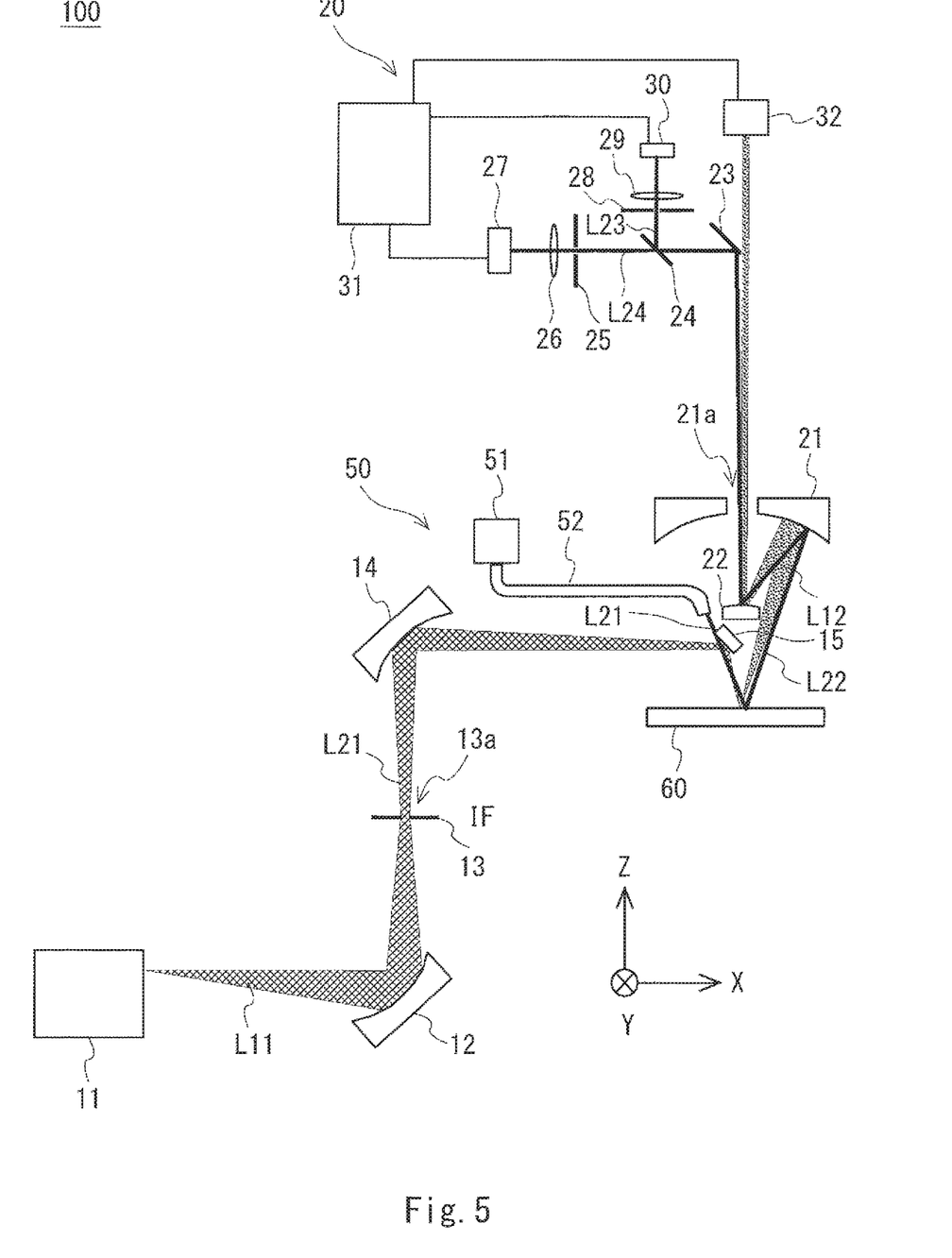
FIG. 5 shows a configuration of an inspection apparatus according to a second exemplary embodiment.

An inspection apparatus and its focus adjustment method according to this exemplary embodiment are explained with reference to FIG. 5. FIG. 5 shows a configuration of an inspection apparatus according to a second exemplary embodiment. Note that the configuration of the second exemplary embodiment differs from that of the first exemplary embodiment in regard to an AF illumination optical system 50 for applying (i.e., emitting) AF light to the EUV mask 60. Specifically, the AF illumination optical system 50 includes an AF light source 51 and an optical fiber 52 in this exemplary embodiment. That is, the AF light source 51 and the optical fiber 52 are provided in place of the AF light source 16. Note that the configuration other than the AF illumination optical system 50 of the second exemplary embodiment is similar to that of the first exemplary embodiment and therefore its explanation is omitted.

AF light emitted from the AF light source 51 propagates through the optical fiber 52 and is incident on the EUV mask 60. The end face of the optical fiber 52 from which the AF light enters is disposed near the AF light source 51 and the end face from which the AF light is output is disposed near the dropping mirror 15. Further, the AF light L21, which has propagated through the optical fiber 52, is incident on the EUV mask 60 from outside of the dropping mirror 15. That is, in this exemplary embodiment, the AF light L21 is incident on the EUV mask 60 without being reflected on the dropping mirror 15.

Even by the above-described configuration, the focus point can be adjusted as in the case of the first exemplary embodiment. Therefore, it is possible to appropriately adjust the focus with a simple configuration. Further, in this exemplary embodiment, it is possible to adjust the incident place of the AF light L21 on the EUV mask 60 by changing the place and the angle of the optical fiber 52. For example, the optical fiber 52 can be disposed so that the incident place of the AF light L21 coincides with the incident place of the EUV light L11 on the EUV mask 60. In this way, it is possible to adjust the focal point based on the AF light reflected on the inspection area. Therefore, it is possible to adjust the focus more accurately. Needless to say, the incident place of the AF light L21 may be shifted from the incident place of the EUV light L11 on the EUV mask 60 as in the case of the first exemplary embodiment.

Note that an example in which the EUV mask 60 with the pellicle 66 disposed thereon is inspected is explained above. However, the EUV mask 60 to be inspected may be an EUV mask 60 including no pellicle 66. That is, the EUV mask 60 to be inspected may be any EUV mask 60 including an absorption film 64 and a multilayer reflection film 62 disposed thereon.

Although the mirror 23, which is disposed only on the optical path of the AF light L22, is used as the branching means for branching (i.e., separating) the AF light L22 from the EUV light L12 reflected on the convex mirror 22 in the above explanation, the branching means is not limited to any particular means. For example, a dichroic mirror or the like that reflects one of the EUV light L12 and the AF light L22 and lets the other light pass therethrough may be used.

Further, the AF light may have a single wavelength or may have a plurality of wavelengths, provided that they are in the range from 450 nm to 650 nm. For example, the AF light source 16 or 51 may include a first light source that generates light having a wavelength at which the reflectivity of the multilayer reflection film 62 is higher than that of the absorption film 64 and a second light source that generates light having a wavelength at which the reflectivity of the multilayer reflection film 62 is lower than that of the absorption film 64. In this case, it is possible to make the amounts of AF light reflected on the multilayer reflection film 62 and the absorption film 64 equal to each other by adjusting the amounts of light emitted from the first and second light sources. That is, the amount of detected AF light is unchanged regardless of whether the AF light is incident on the absorption film 64 or on the multilayer reflection film 62. As a result, the focus can be adjusted more accurately.

Although exemplary embodiments according to the present invention have been explained above, the present invention also includes various modifications that do not substantially impair the purposes and the advantages of the present invention. Further, the above-described exemplary embodiments should not be used to limit the scope of the present invention.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

The invention claimed is:

1. An inspection apparatus comprising:
   an EUV (Extremely Ultraviolet) light source configured to generate EUV light;
   an illumination optical system provided to apply the EUV light to an EUV mask comprising a multilayer reflection film and an absorption film;
   a concave mirror with a hole formed therein, the concave mirror with the hole being configured to reflect the EUV light reflected on the EUV mask;
   a convex mirror configured to reflect the EUV light reflected on the concave mirror with the hole toward the hole of the concave mirror with the hole;
   an image pickup device configured to detect the EUV light reflected on the convex mirror and thereby take an image of the EUV mask;
   an Auto Focus light source configured to generate Auto Focus light having a wavelength of 450 nm to 650 nm;
   an Auto Focus photodetector configured to detect the Auto Focus light reflected on the EUV mask through the concave mirror with the hole and the convex mirror; and
   an adjustment unit configured to adjust a focus point of the EUV light on the EUV mask based on a detection result of the Auto Focus photodetector,
   wherein the Auto Focus light is incident on an outer side of an incident place on which the EUV light is incident on a reflection surface of the concave mirror with the hole.

2. The inspection apparatus according to claim 1, wherein the illumination optical system comprises a dropping mirror disposed directly above the EUV mask, the dropping mirror being configured to reflect the EUV light emitted from the EUV light source toward the EUV mask, and
   the Auto Focus light is reflected on the dropping mirror and then incident on the EUV mask.

3. The inspection apparatus according to claim 2, wherein a stop is disposed in a place conjugate with the EUV mask in the illumination optical system, and
   the Auto Focus light source is disposed on a rear side of the stop.

4. The inspection apparatus according to claim 1, wherein the illumination optical system comprises a dropping mirror disposed directly above the EUV mask, the dropping mirror being configured to reflect the EUV light emitted from the EUV light source toward the EUV mask, and
   the Auto Focus light is incident on the EUV mask from outside of the dropping mirror.

5. The inspection apparatus according to claim 4, wherein an incident place on which the Auto Focus light is incident coincides with the incident place on which the EUV light is incident on the EUV mask.

6. The inspection apparatus according to claim 1, wherein an incident place on which the Auto Focus light is incident is deviated from the incident place on which the EUV light is incident on the EUV mask.

7. The inspection apparatus according to claim 1, wherein a pellicle formed of a material containing silicon is provided on the EUV mask.

8. A focus adjustment method for an inspection apparatus, the inspection apparatus comprising:
   an EUV light source configured to generate EUV light;
   an illumination optical system provided to apply the EUV light to an EUV mask comprising a multilayer reflection film and an absorption film;
   a concave mirror with a hole formed therein, the concave mirror with the hole being configured to reflect the EUV light reflected on the EUV mask;
   a convex mirror configured to reflect the EUV light reflected on the concave mirror with the hole toward the hole of the concave mirror with the hole;
   an image pickup device configured to detect the EUV light reflected on the convex mirror and thereby take an image of the EUV mask; and
   an Auto Focus light source configured to generate Auto Focus light having a wavelength of 450 nm to 650 nm,
   the focus adjustment method comprising:
   a step of detecting the Auto Focus light reflected on the EUV mask through the concave mirror with the hole and the convex mirror; and
   a step of adjusting a focus point of the EUV light on the EUV mask based on a detection result of the Auto Focus photodetector,
   wherein the Auto Focus light is incident on an outer side of an incident place on which the EUV light is incident on a reflection surface of the concave mirror with the hole.

9. The focus adjustment method according to claim 8, wherein
   the illumination optical system comprises a dropping mirror disposed directly above the EUV mask, the dropping mirror being configured to reflect the EUV light emitted from the EUV light source toward the EUV mask, and
   the Auto Focus light is reflected on the dropping mirror and then incident on the EUV mask.

10. The focus adjustment method according to claim 9, wherein
- a stop is disposed in a place conjugate with the EUV mask in the illumination optical system, and
- the Auto Focus light source is disposed on a rear side of the stop.

11. The focus adjustment method according to claim 8, wherein
- the illumination optical system comprises a dropping mirror disposed directly above the EUV mask, the dropping mirror being configured to reflect the EUV light emitted from the EUV light source toward the EUV mask, and
- the Auto Focus light is incident on the EUV mask from outside of the dropping mirror.

12. The focus adjustment method according to claim 11, wherein the incident place on which the Auto Focus light is incident coincides with the incident place on which the EUV light is incident on the EUV mask.

13. The focus adjustment method according to claim 8, wherein the incident place on which the Auto Focus light is incident is deviated from the incident place on which the EUV light is incident on the EUV mask.

14. The focus adjustment method according to claim 8, wherein a pellicle formed of a material containing silicon is provided on the EUV mask.

\* \* \* \* \*